United States Patent [19]

Skalsky et al.

[11] Patent Number: 4,784,161
[45] Date of Patent: Nov. 15, 1988

[54] POROUS PACEMAKER ELECTRODE TIP USING A POROUS SUBSTRATE

[75] Inventors: Michael Skalsky, Waverly; Zoran Millijasevic, Elanora Heights; Akira Nakazawa, Balmain; Gerhard Gotthardt, Castle Hill, all of Australia

[73] Assignee: Telectronics, N.V., Netherlands Antilles

[21] Appl. No.: 933,998

[22] Filed: Nov. 24, 1986

[51] Int. Cl.$^4$ .............................................. A61N 1/05
[52] U.S. Cl. .................................. 128/785; 128/786; 128/419 P
[58] Field of Search .............................. 128/784–786, 128/642, 419 P

[56] References Cited

U.S. PATENT DOCUMENTS

| | | | |
|---|---|---|---|
| 3,911,928 | 10/1975 | Lagergren | 128/786 |
| 4,011,861 | 3/1977 | Enger | 128/419 P X |
| 4,149,542 | 4/1979 | Thoren | 128/786 |
| 4,407,302 | 10/1983 | Hishorn et al. | 128/784 |
| 4,408,604 | 10/1983 | Hirshorn et al. | 128/785 |
| 4,502,492 | 3/1985 | Bornzin | 128/785 |
| 4,506,680 | 3/1985 | Stokes | 128/786 |

FOREIGN PATENT DOCUMENTS 0047013 3/1982 European Pat. Off. .
8002231 10/1980 PCT Int'l Appl. ................. 128/786

Primary Examiner—Lee S. Cohen
Attorney, Agent, or Firm—Finnegan, Henderson, Farabow, Garrett & Dunner

[57] ABSTRACT

An implantable stimulating lead for a cardiac pacemaker has a distal tip having a surface area adapted to physically contact heart tissue for pacing the heart tissue, sensing heart contractions and promoting tissue ingrowth. The distal tip includes a conductive electrode and a porous non-conductive substrate, which together define the surface area of the distal tip. The conductive electrode and porous substrate are provided as first and second members, although the surface area of each is adapted to present a singular, smooth distal tip region for the electrode lead.

2 Claims, 7 Drawing Sheets

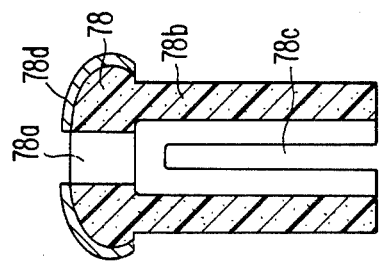
FIG. 8.
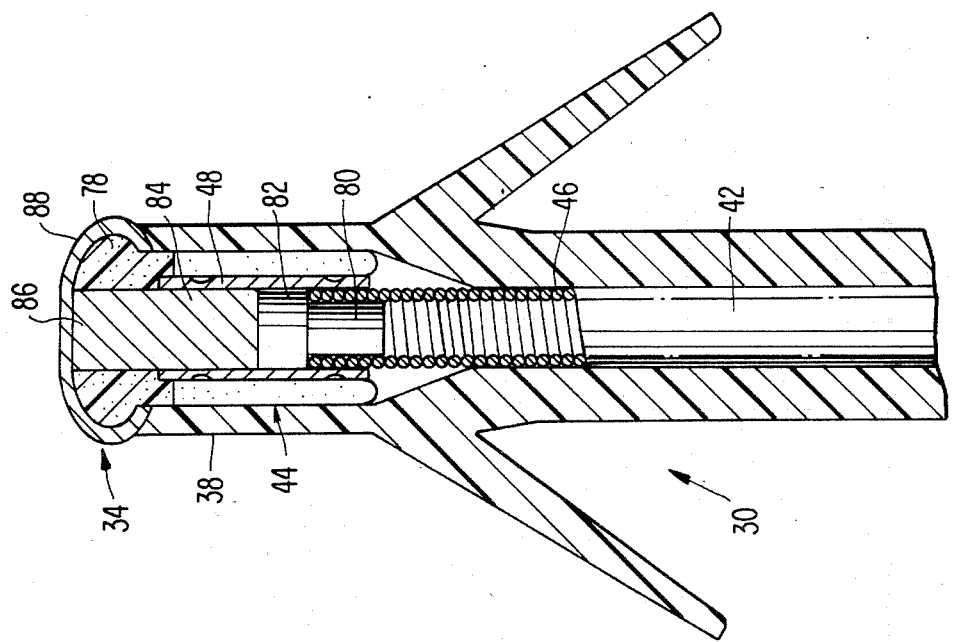
FIG. 7.
FIG. 6.

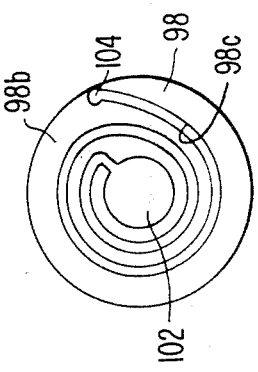
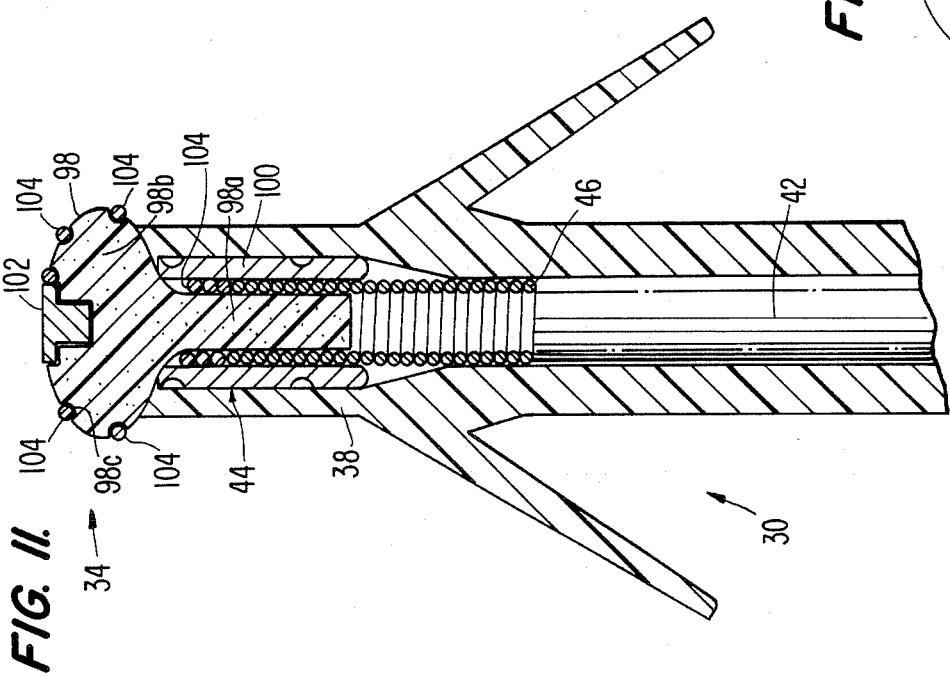
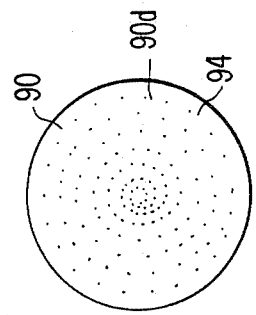
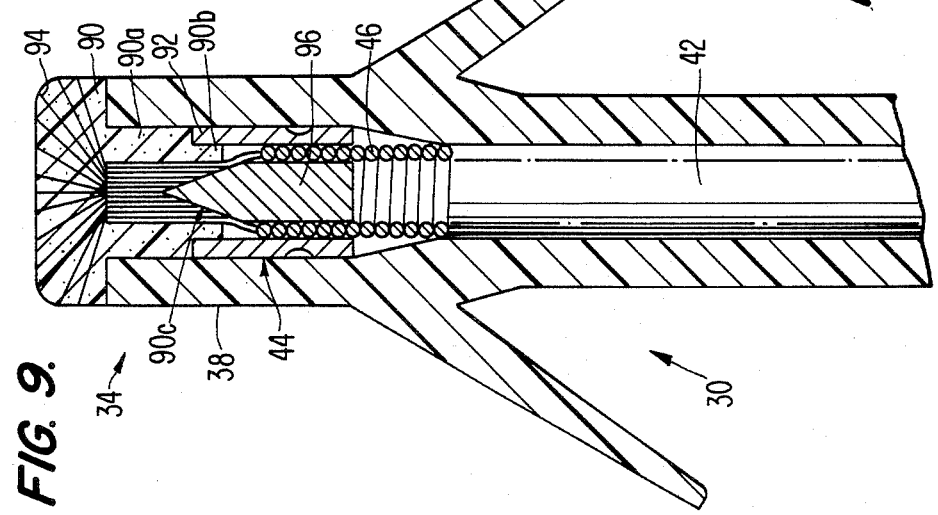

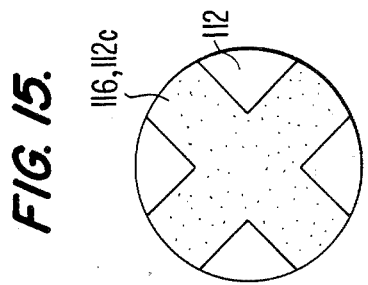
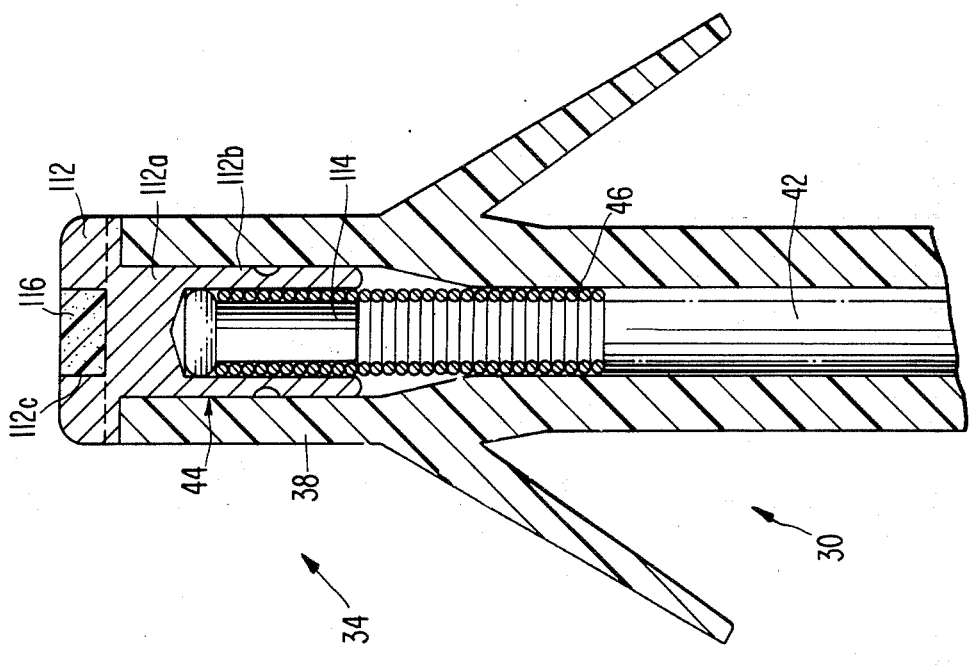
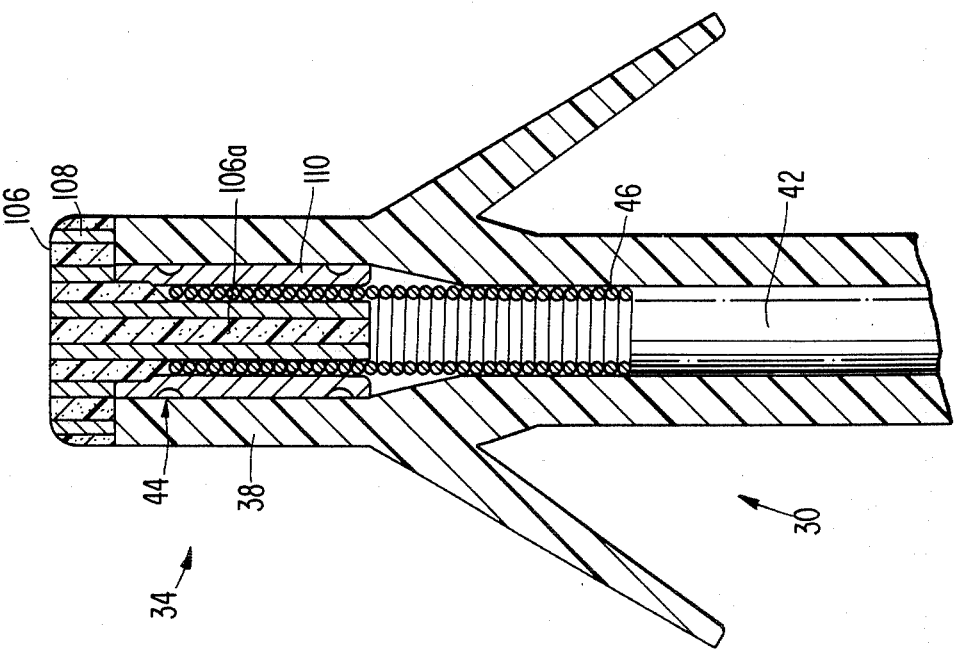

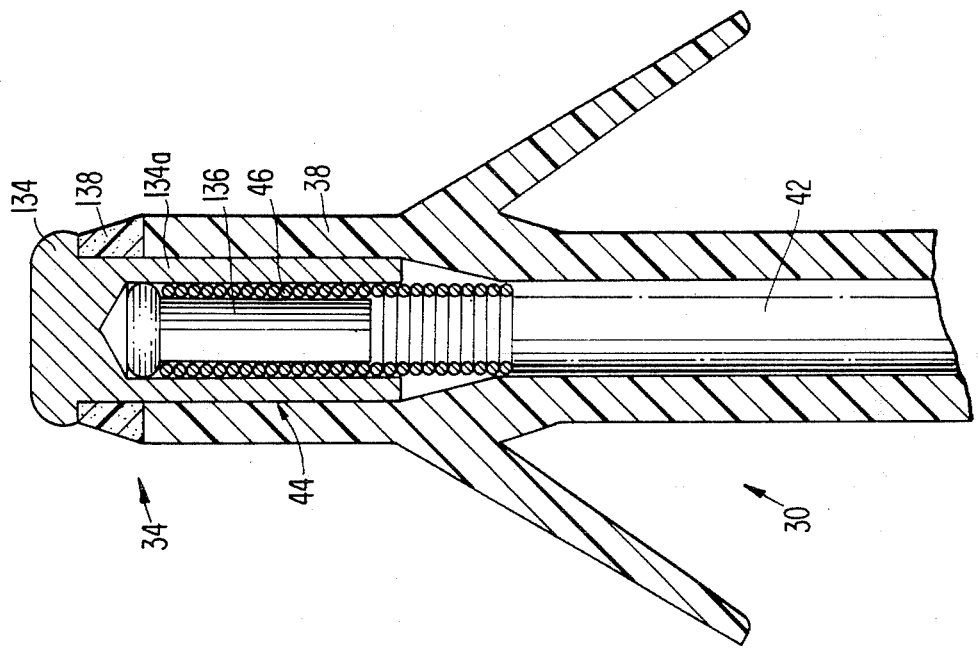
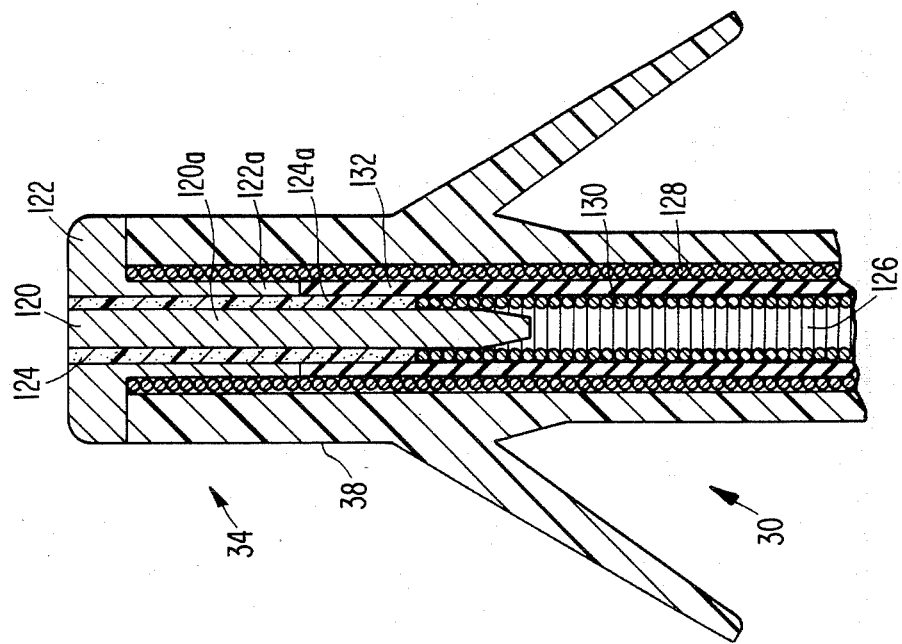

POROUS PACEMAKER ELECTRODE TIP USING A POROUS SUBSTRATE

BACKGROUND OF THE INVENTION

The present invention relates to an implantable stimulating lead for a cardiac pacemaker.

In physiological terms, a cardiac pacemaker must be capable of generating a signal with a sufficient magnitude to depolarise the excitable cells of tissue within the heart. This signal is delivered to the cardiac tissue of the the heart via a lead which has an electrode tip in contact with the heart tissue. Electrode size and shape, tissue electrolyte conductivity, and the distance separating the electrode from the adjacent tissue are factors in determining the energy required of the pacemaker. Many of these factors are affected by the particular geometry and material composition of the electrode, as explained hereinbelow.

For example, current drain in a constant voltage pacemaker is determined by a combination of the impedance of the pacemaker circuitry, the nature of the electrode resistance and the characteristics of the electrode tip interface with the surrounding tissue. The most significant frequency component of the pacing pulse generated by the pacemaker is on the order of 1 KHz. At this frequency, most of the impedance to the pacing pulses is due to the bulk of the electrode, i.e. "spreading" impedance.

The impedance presented to the pulse generated by the pacemaker is a function of the geometric, i.e. macroscopic, surface area of the electrode and the radius of the electrode. For example, an electrode having a small radius will have a higher pacing impedance and smaller current drain than a similarly shaped electrode of a larger radius. All of these factors must be considered in maximizing the design of an electrode for purposes of effectively delivering pulses so as to pace operation of the heart.

In addition to this pacing function, the electrode must also provide for sensing of heart activity, e.g. for determining the presence of aberrant behavior so that pacing operation will be initiated. In this sensing operation, the most significant sensed frequency components of atrial or ventricular signals are in the bandwidth of 20–100 Hz. In this region, interface impedance of the electrode with the surrounding cardiac tissue becomes significant. This impedance is determined by the microscopic surface area of the electrode and is established within a few microns of the electrode's surface. The microscopic surface area, or microstructure of an electrode, is the total surface area, including all microscopic ridges, cracks, crevices and indentations on the stimulating surface of the electrode.

Another factor of concern in connection with maximizing operation of pacemaker electrodes relates to pacing threshold. The pacing, or stimulating, threshold is a reflection of the energy required for a pulse to initiate a contraction in the cardiac tissue. This stimulation threshold rises for weeks after the implant of a pacemaker lead as a result of an increase in the spacing between the electrode and the excitable tissue. The spacing occurs due to the development of a fibrous capsule around the electrode tip which is reported to be between 0.3 mm and 3 mm thick. There are indications that lower long term pacing thresholds result with more reliable fixation of the electrode to the surrounding tissue.

In view of the above characteristics of an electrode for a cardiac pacemaker, an electrode should have a small geometric macroscopic surface area and a small radius in order to provide high pacing impedance and low current drain. However, to achieve low sensing impedance and thus enhance sensing, the same electrode tip should have a large microsurface area or enhanced microstructure. Furthermore, to provide lower long term pacing thresholds, the electrode should also provide secure and reliable attachment to the heart wall with minimal fibrous capsule formation.

Heretofore, in order to achieve the foregoing, pacemaker leads were provided with an electrode that is both porous and conductive. In devices of this type, the conductive characteristics were adapted to provide the electrical functions, i.e. sensing and pacing operations, while the porous characteristics were relied upon to facilitate attachment to the cardiac tissue by promoting tissue ingrowth. Such devices suffer in design, however, in that the single surface area of the electrode must satisfy the various, and oftimes contradictory, design demands as outlined above.

Specifically, although electrodes can be designed that are satisfactory for the purposes of pacing and sensing, the desire for a porous conductive tip structure is often difficult to reconcile. Furthermore, such small geometric surface areas are difficult to construct, and it is necessary to limit any reduction in electrode diameter in order to minimize the risk of cardiac wall perforation. An additional problem results in that stimulation electrodes are generally made of expensive metals (pt/Iridium, Pt), so any additional conductive material required in making the external stimulation surface and tissue ingrowth structure into one unit significantly increases the cost of manufacture.

SUMMARY OF THE INVENTION

It is therefore an object of the present invention to design an implantable electrode lead for a cardiac pacemaker having high pacing impedance and, thus, low current drain.

Another object of the present invention is to provide a cardiac pacemaker electrode lead with low sensing impedance for enhanced sensing.

A further object of the present invention is to provide a cardiac pacemaker electrode lead which results in good, reliable attachment to the heart wall with minimal fibrous capsule formation, and therefore provides lower long-term pacing thresholds.

To achieve the foregoing objects, and in accordance with the purposes of the invention as embodied and broadly described herein, an implantable stimulating lead is provided for a cardiac pacemaker having a proximal end adapted to be connected to a pulse generator, and a distal tip region having a surface area adapted to physical contact heart tissue for stimulating heart tissue, sensing heart contractions and promoting tissue ingrowth, the distal tip region comprising a first member defining a conductive electrode having a conductive surface area forming a first portion of the distal tip surface area forming a second portion of said distal tip surface area to stimulate heart tissue and sense heart contractions; and a second member defining a nonconductive substrate having a porous surface area, forming a second portion of said distal tip surface area to promote tissue ingrowth and attachment of the distal tip region to the heart tissue.

In other aspects, the lead in accordance with the present invention preferably comprises means disposed in the tip region for eluting bioactive agent into heart tissue adjacent the distal tip region to reduce tissue inflammation response.

Additional objects and advantages of the invention will be set forth in the description which follows. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a preferred embodiment of the invention and, together with the general description given above and the detailed description of the preferred embodiment given below, serve to explain the principles of the invention.

FIG. 6 is a fragmentary sectional view of an implantable lead, illustrating a distal tip region in accordance with a second preferred embodiment of the present invention;

FIG. 7 is a fragmentary sectional view of an implantable lead, illustrating a distal tip region in accordance with a third preferred embodiment of the present invention:

FIG. 8 is a sectional view of the porous substrate of FIG. 7;

FIG. 9 is a fragmentary sectional view of an implantable lead, illustrating a distal tip region in accordance with a fourth preferred embodiment of the present invention;

FIG. 10 is a top plan view with the tines removed of the distal tip of FIG. 9;

FIG. 11 is a fragmentary sectional view of an implantable lead, illustrating a distal tip region in accordance with a fifth preferred embodiment of the present invention;

FIG. 12 is a top plan view illustrating the surface area of the distal tip of FIG. 11;

FIG. 13 is a fragmentary sectional view of an implantable lead, illustrating a distal tip region in accordance with a sixth preferred embodiment of the present invention;

FIG. 14 is a fragmentary sectional view of an implantable lead, illustrating a distal tip region in accordance with a seventh preferred embodiment of the present invention;

FIG. 15 is a top plan view illustrating surface area of the distal tip of FIG. 14;

FIG. 21 is a fragmentary sectional view of an implantable lead, illustrating a distal tip region in accordance with an eighth preferred embodiment of the present invention;

FIG. 23 is a fragmentary of an implantable lead, illustrating a distal tip region in accordance with a ninth preferred embodiment of the present invention;

DESCRIPTION OF THE PREFERRED EMBODIMENTS

Figure 1:
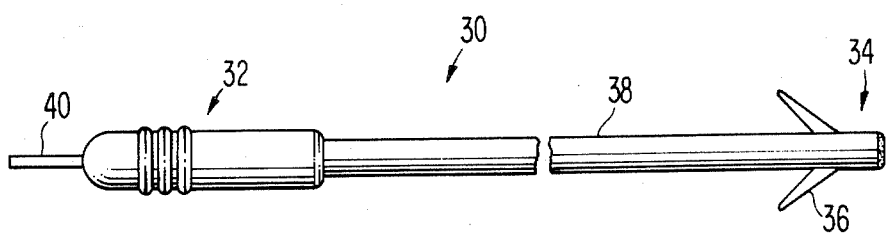
FIG. 1 illustrates a typical implantable electrode lead suited to incorporate the present invention.

Reference will now be made in detail to the presently preferred embodiments of the invention as illustrated in the accompanying drawings. Throughout the drawings, the reference characters are used to indicate like elements.

FIG. 1 shows an implantable stimulating lead 30 for a cardiac pacemaker (not shown). Lead 30 comprises a hollow shaft having a proximal end 32 of conventional construction for connection to the pacemaker; a distal tip region 34 for electrically stimulating heart tissue, sensing heart contractions and promoting tissue ingrowth; a tine molding 36 for anchoring lead 30 within the heart; insulation molding 38 for electrically insulating lead 30; and a terminal 40 for establishing an electrical connection between the pulse generator and the distal tip region 34. Terminal 40 is electrically coupled to another conductor, such as a helically wound wire (not shown in FIG. 1), which passes axially through the length of lead 30.

Insulation body 38 and tine molding 36 are commonly made of silicon rubber or polyurethane (such as pellethane 2363-90A); however, other suitable materials may be employed without departing from the spirit or scope of the invention.

In the discussion which follows, various parts of lead 30 are described in terms of a "distal" direction, which is towards distal tip region 34 and a "proximal" direction, which is towards proximal end 32.

Figure 2:
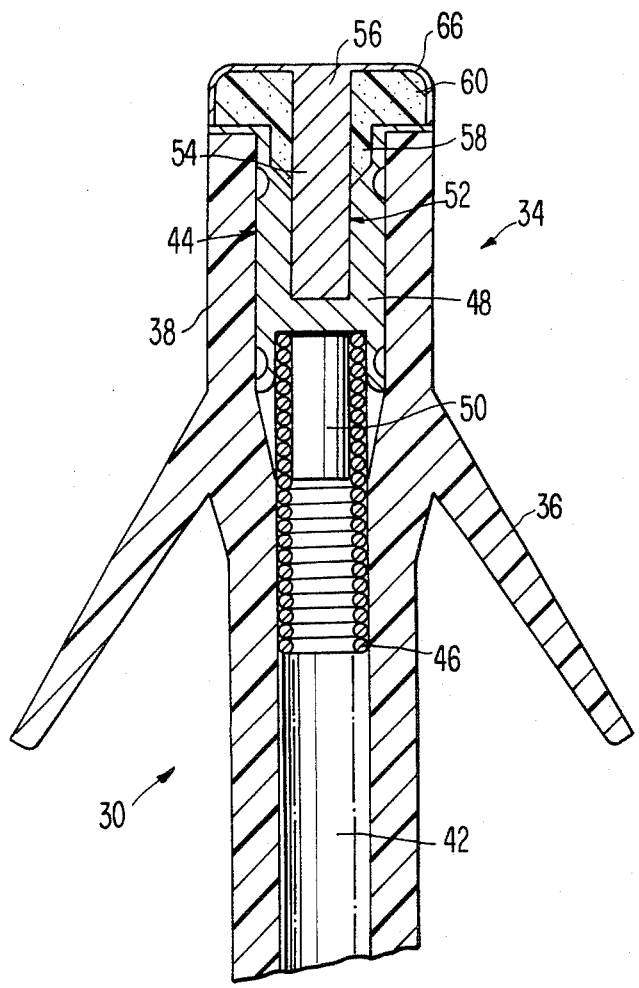
FIG. 2 is an elarged fragmentary sectional view of the implantable lead of FIG. 1 illustrating a distal tip region in accordance with a first preferred embodiment of the present invention.

FIG. 2 is a fragmentary sectional view of implantable lead 30, particularly distal tip region 34, in accordance with a first preferred embodiment of the present invention. According to the invention, a first member is provided defining a conductive electrode having a conductive surface area forming a first portion of the distal tip surface area. As illustrated in FIG. 2, this first member is identified by reference character 56. Also according to the invention, a second member is provided defining a non-conductive porous substrate having a porous surface area. As illustrated in FIG. 2, this second member is identified by reference character 60. The particular construction of these two members will be apparent from the following discussion of the overall structure of the electrode lead shown in FIG. 2.

Lead 30 comprises a central axial passage 42. Near its distal end, passage 42 widens and leads to an axial space 44. Axial space 44 opens to the outside of lead 30 at the distal end of molding 38 ahead of tine molding 36. A helical conductor 46 is disposed within axial passage 42 and extends at one end into axial space 44; at its other end, helical conductor 46 may be coupled to terminal 40 (FIG. 1). Helical conductor 46 is secured in axial space 44 by a crimp tube 48. Crimp tube 48 is preferably made of a ductile, inert, metallic conductor, such as PT, PT/IR or TI. A support pin 50, preferably of stainless steel or MP35N, is centrally disposed in axial space 42 in order to insure that the helical conductor 46 is satisfactorily engaged by crimp tube 48, and that an electrical connection is established between these elements.

Crimp tube 48 preferably extends the length of axial space 42 and ends flush with the distal end of insulation molding 38. At its distal end, crimp tube 48 has an internal passageway 52 for a shaft 54 of conductive electrode 56 and a shaft 58 of non-conductive porous substrate 60.

Figure 3:
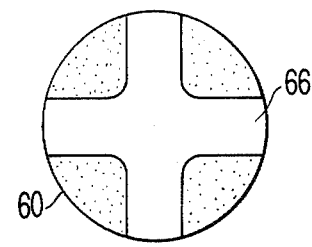
FIG. 3 is a top plan view illustrating the surface area of the distal tip of FIG. 2.
Figure 4:
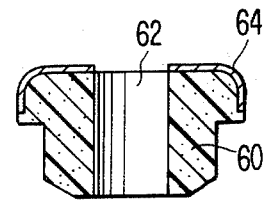
FIG. 4 is a sectional view of a porous substrate of the distal tip region of FIG. 2, shown without the conductive electrode member.

As shown in FIGS. 3 and 4, porous substrate 60 has a central passage 62 for containing shaft 54 of electrode 56. Porous substrate 60 also comprises grooves 64 for holding discrete portions or "leaves" 66 of electrode 56. Thus, when substrate 60 is engaged by crimp tube 48, substrate 60 is seated on the distal end of insulation molding 38. Electrode 56 is inserted into cavity 62 via shaft 54, and both electrode 56 and porous substrate 60 are securely engaged by crimp tube 48.

Electrode leaves 66, disposed in grooves 64, form a conductive electrode surface that is flush with the porous surface of porous substrate 60. Collectively, the conductive electrode surface and the porous surface comprise the surface region of the distal tip of the electrode lead of the invention.

Top and side views of the electrode surface of leaves 66 and porous surface 60 are shown in FIGS. 3 and 4, respectively. Leaves 66 preferably radiate from shaft 58 in a cross shape and are bent around the sides of porous part 60 in grooves 64 so as to conform thereto in shape.

Porous substrate 60 is preferably made of a non-conductive, inert bio-compatible material such as ceramic or polymer. Possible materials for the porous substrate are alumina, silicon nitride, barium titanate, partially stabilized zirconia, polypropylene, polyethylene, silicon rubber, polyurethane or an equivalent material. Substrate 60 may be made porous by using techniques such as laser drilling, sintering, foaming, etc. to result in pores of 5–300 microns for allowing optimized tissue ingrowth.

In U.S. Pat. No. 4,506,680, an electrode is described containing drug eluting means to minimize tissue inflammation response. The teaching of that patent is expressly incorporated herein by reference. In the present invention, drug eluting means may be disposed directly within non-conductive porous substrate 60. As discussed later with respect to the embodiment illustrated in FIGS. 24–25, porous substrate 60 can also be used as a diffuser for the bioactive agent if a source of agent is contained within distal tip 4.

Figure 5:
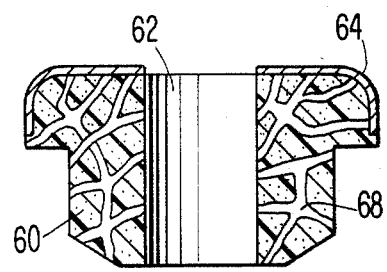
FIG. 5 is a sectional view of an alternate embodiment of the porous substrate according to the present invention capable of being incorporated in the distal tip region of FIG. 2.

In one embodiment according to the invention, bioactive agent is suspended in an aqueous or organic solvent medium and allowed to permeate into the porous structure of porous substrate 60 by capillary action only. Agent could also be loaded in substrate 60 by first evacuating the substrate 60 and then exposing it to a solution of bioactive agent. Alternatively, the agent can be introduced under pressure or moulded into a polymer matrix to form bioactive agent containing channels 68, as shown in FIG. 5. Another variation is to suspend the agent in a preferably biodegradable polymer such as poly-glycolic acid or its derivatives or equally suitable materials, and introduce the suspension into porous substrate 60 under pressure. As the polymer is biodegraded, or when the drug is released, removal of the polymer/drug material opens up pores to allow tissue in-growth. One skilled in the art will readily appreciate that bioactive agent elution means may be incorporated in the porous parts of any of the following preferred embodiments.

Electrode leaves 66 are preferably made of a thin (50-300 microns) biocompatible conductive material. The electrode material may be platinum, platinum-/iridium, titanium, or an equivalent material. The cross shape of leaves 66, as seen in FIG. 3, reduces the electrode surface area of leaves 66 to about 3–4 $mm^2$, according to a preferred embodiment. The total surface area of the distal tip 34 remains larger than this figure, however, due to the porous surface area contributed by porous substrate 60. The described construction thus minimizes the risk of heart wall perforation because a relatively large total surface area is in direct contact with the heart tissue.

It should be appreciated that shapes for leaves 66 other than a cross are possible and are incorporated into the present invention. As is discussed above, leaves 66 are disposed in grooves 64 of porous substrate 60 so as to present an uninterrupted surface to the adjacent tissue.

Electrode 56 can be treated to create a low polarizing microstructure. Microstructure can be produced by glass bead blasting, electrochemical deposition, ion beam texturing, sputter etching or deposition. The microstructure preferably comprises a coating produced by IMI-Marston Wolverhampton, England, known as "K" type.

It should be noted that methods of joining the metallic parts of the present invention other than crimping, such as welding, are possible. Porous substrate 60 may also be fixed to electrode 56 by reaction fusion bonding or by the use of adhesives.

Electrode leaves 66 may also comprise a thin coating of suitable conducting material applied directly to porous substrate 60 using electrochemical or sputter deposition as described for producing microstructure. Yet another alternative for producing electrode leaves 66 is to sinter together ceramic and metal powder or spheres and then remove a desired amount of surface metal using photoetching, or an equivalent technique to give a desired electrode shape and electrode surface area.

From the foregoing, it can be appreciated that an electrode is provided having a first member 56 which is conductive and a second member 60 which is nonconductive and porous. The first member 56 provides the electrical characteristics necessary for sensing and pacing operations, whereas the second member 60 provides for tissue ingrowth to facilitate secure placement of the electrode. Together, the exposed surface areas of first and second member 56, 60 comprise the overall surface area of the distal tip 34 of the pacemaker electrode lead 30. As discussed hereinbelow, various embodiments of a pacemaker electrode lead are discussed which are considered to be within the spirit and scope of the present invention.

FIG. 6 is a fragmentary sectional view of implantable lead 30, particularly distal tip 34, in accordance with a second preferred embodiment of the present invention. Crimp tube 70 of the embodiment of FIG. 6 includes an annular flange 72. Annular flange 72 serves as a seat for porous substrate 60 and provides an electrical connection between crimp tube 70 and electrode leaves 66 near the outer periphery of substrate 60 and insulation molding 38. Crimp tube 70 preferably comprises tapered recess 74 for mechanically engaging a corresponding taper on shaft 76 of electrode 56.

FIG. 7 is a fragmentary sectional view of implantable lead 30, particularly distal tip region 34, in accordance with a third preferred embodiment of the present invention. FIG. 8 is a cross-sectional view of porous part 78 of the third preferred embodiment.

As is shown in FIG. 8, porous substrate 78 comprises an axial cavity 78a extending along the entire length of porous substrate 78. The porous substrate 78 also comprises an extended shaft 78b for extending substantially into axial space 44 of insulation body 38. Porous substrate 78 also comprises two slots 78c (only one of which is shown in FIG. 6), preferably positioned 180° apart, which extend along most of the length of shaft 78b. Slots 78c facilitate the crimping of crimp tube 48, and thus the assembly of distal tip region 34.

The distal tip region 34 of FIG. 8 is assembled as follows. Crimp tube 48, preferably comprising a cylindrical sheath, is crimped to helical conductor 46 with the aid of support pin 80 disposed within helical conductor 46. A sealing plug 82 is placed within crimp tube 48 above helical conductor 46 and support pin 80. Electrode shaft 84 of electrode 86 is inserted into the distal end of cavity 78a of porous substrate 78. Crimp tube 48 is crimped onto shaft 84 to establish mechanical and electrical connection between shaft 84 and crimp tube 48. Electrode 86 is further mechanically fixed to porous substrate 78 by folding or rolling conductive electrode leaves 88 substantially around the distal end of porous substrate 78 within grooves 78d. Finally, the distal tip 34 may be filled with an adhesive, such as silicone rubber, polyurethane or epoxy to provide sealing and additional mechanical fixation.

FIG. 9 is a fragmentary sectional view of an implantable lead 30, particularly distal tip region 34, in accordance with a fourth preferred embodiment to the present invention. A cap of mushroom-shaped porous substrate 90 fits on the distal end of insulation body 38. Porous substrate 90 has a shaft 90a which extends into axial space 44. Shaft 90a has an extension 90b of reduced diameter which is surrounded by and engaged by cylindrical crimp tube 92. Conical recess 90c is provided within shaft 90a and positioned along the central axis of porous substrate 90. A plurality of fibers or wires 94 pass from conical recess 90c through shaft 90a and radiate outward to the cap of porous substrate 90. The plurality of wires 94 extend through substrate 90 so that their exposed ends collectively form an electrode surface area at the surface of porous substrate 90.

As is seen in FIG. 10, the plurality of wires 94 emerge at the surface of porous substrate 90 so as to form an electrode surface area. The space between wires 94 defines a porous surface area 90d.

A support pin 96 is disposed partially within the distal end of helical conductor 46. Crimp tube 92 mechanically fixes helical conductor 46 to support pin 96 and establishes an electrical connection therewith. Support pin 96 has a conical tip for engaging the lengths of wires 94 extending through substrate 90 into the conical recess 90c. Support pin 96 thereby establishes an electrical connection between helical conductor 46 and wires 94.

Porous substrate 90 may be mechanically joined to crimp tube 92 by compression or braising using methodology commonly applied in the manufacture of ceramic feedthroughs, or, if substrate 90 is made of a polymer, by using an appropriate adhesive. Modifications such as these are considered to be within the spirit and scope of the present invention.

Electrode fibers 94 may be made of platinum, platinumliridium, carbon or equivalent materials. Fibers 94 are preferably introduced into porous substrate 90 prior to final fabrication of substrate 90 by sintering or molding.

FIG. 11 is a fragmentary sectional view of an implantable lead 30, particulary distal tip region 34 in accordance with a fifth preferred embodiment of the present invention. Porous substrate 98 includes a shaft 98a extending substantially the length of axial space 44. Helical conductor 46 surrounds shaft 98a and a crimp tube 100, preferably formed of a cylindrical sheath, surrounds helical conductor 46 in axial space 44. Crimp tube 100 mechanically fastens helical conductor 46 to shaft 98a, and fastens conductor 46 and shaft 98a to molding 38.

Porous substrate 98 has a bulbous protrusion 98b which is seated on the distal end of molding 38. An electrode comprising a plug 102 is centrally disposed at the distal end of porous substrate 98. Electrically conductive plug 102 serves to fix an electrode coil 104 to the bulbous protrusion 98b of porous substrate 98. Electrical coil 104 is preferably disposed in a spiral groove 98c on the surface of porous substrate 98. Electrode coil 104 thus spirals away from plug 102 and down the bulbous portion 98b of porous substrate 98 outside of molding 38. Electrode coil 104 passes into axial space 44 and is wound partially around shaft 98a. Crimp tube 100 fastens electrode coil 104 to shaft 98a and thereby establishes an electrical connection between conductors 46 and coil 104.

FIG. 13 is a fragmentary sectional view of an implantable lead 30, particularly distal tip region 34, in accordance with a sixth preferred embodiment of the present invention. The sixth preferred embodiment comprises a porous substrate 106 having a central porous shaft 106a which extends the length of axial space 44 and past the distal end of molding 38. An electrode foil 108 is wound spirally within, and laminated to the porous substrate 106. Foil 108 preferably spirals radially away from the center of porous substrate 106, forming a laminated rolled structure of alternating layers of foil 108 and porous material 106. Helical conductor 46 surrounds winding 106 in axial space 44 to establish an electrical connection therewith. A crimp tube 110 fixes conductor 46 to a section of winding 108 surrounding shaft 106a of substrate 106. Crimp tube 110 preferably extends the length of axial space 44.

FIG. 14 is a fragmentary sectional view of an implantable lead 30, particularly distal tip region 34, in accordance with a seventh preferred embodiment of the present invention. The seventh embodiment comprises a generally mushroom-shaped electrode 112 having a shaft 112a extending into axial space 44. The walls 112b of shaft 112a of electrode 112 function as a crimp tube. Helical conductor 46 fits into the hollow portion defined by walls 112b and is secured by crimping with the aid of a support pin 114. A cross-shaped porous substrate 116 is disposed in cross-shaped cavity 112c provided in the surface of electrode 112, as shown in the exploded view of FIG. 15. Other geometries may be employed, however, without departing from the present invention.

When assembled, electrode 112 and porous substrate 116 present an uninterrupted surface to the surrounding heart tissue. As is seen in FIG. 15, electrode 112 defines an electrode surface for electrically stimulating heart tissue and sensing heart contractions, while porous substrate 116 defines a porous surface area for promoting tissue fixation.

Figure 16:
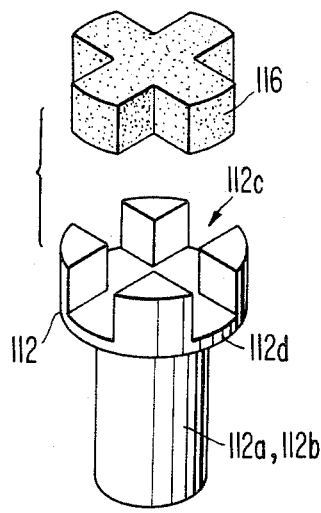
FIG. 16 is an exploded view in perspective of the electrode and porous members of FIG. 15.
Figure 17:
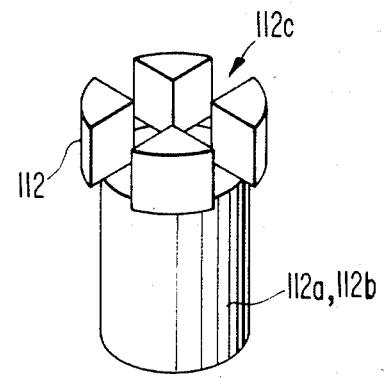
FIG. 17 is a perspective view of an alternate embodiment of the electrode member of FIG. 14.

As is shown in FIG. 16, porous substrate 116 rests on a ledge 112d defining the outer periphery of grooves 112c. Porous element 116 is then fitted into cavity 112c and is seated on ledge 112d. FIG. 17 shows an alternate embodiment of electrode part 112 without ledge 112d.

Figure 18:
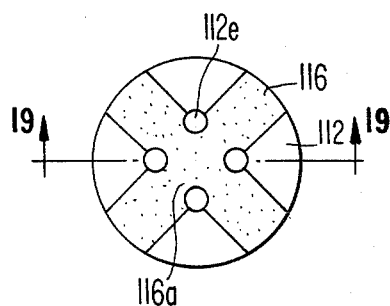
FIG. 18 is a top plan view illustrating the surface area of a second alternate embodiment of the electrode and porous members adapted to be used in the embodiment of FIG. 14.
Figure 19:
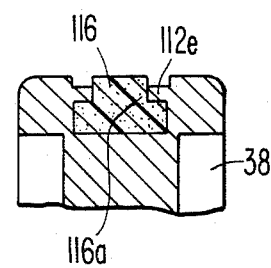
FIG. 19 is a cross sectional view along line 19—19 in FIG. 18.
Figure 20:
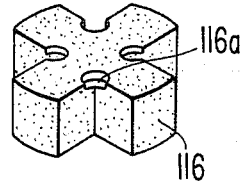
FIG. 20 is a view in perspective of the porous member of FIG. 19.

FIG. 18 is a top view of an embodiment of electrode 112 and porous substrate 116 in which deformed corners 112e of electrode 112 mechanically engage corresponding recesses 116a in porous substrate 116. FIG. 19 is a cross-sectional view of a distal tip region according to FIG. 18 taken along line 19—19. In FIG. 19, deformed corners 112e can be seen engaging recesses 116a. FIG. 20 is a prospective view of the porous part of FIGS. 18 and 19, also showing recesses 116a.

In this seventh embodiment, electrode 112 is preferably made of a solid, biocompatible, conductive material such as platinum, platinum/iridium, titanium, or an equivalent material. Electrode 112 is machine formed to the shape shown in FIG. 16, or alternatively that shown in FIG. 17. The surface of electrode 112, for electrically stimulating heart tissue and sensing heart contractions, can be treated by glass bead texturing, sputter etching or deposition to form a desired microstructure.

Porous substrate 116 can be made of any of the non-conductive bio-compatible materials, such as ceramic or polymer, described hereinabove.

Figure 22:
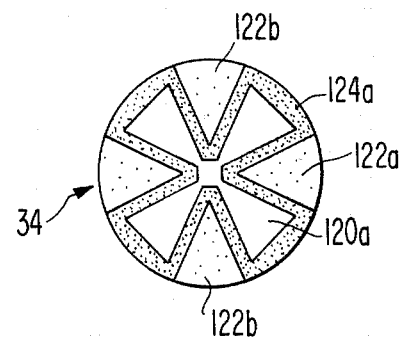
FIG. 22 is a top plan view illustrating the surface area of the distal tip of FIG. 21.

FIG. 21 is a fragmentary sectional view of an implantable lead 30, particularly a distal tip region 34, in accordance with an eighth preferred embodiment of the present invention. FIG. 22 is a top view of the distal tip region 34 according to FIG. 21. As can be seen FIGS. 21 and 22, in the eighth preferred embodiment the electrode is functionally divided into two separate parts according to sensing versus pacing operations. That is, the electrode comprises a pacing electrode 120 and sensing electrode 122. Pacing electrode 120 defines a "maltese cross" shaped pacing surface area 120a, as seen in FIG. 22, and sensing electrode 122 defines four pie-shaped sensing surfaces 122a. Each sensing surface 122a, as seen in FIG. 22, extends from the periphery of the distal tip 34 inwardly between two corresponding pieces of pacing surface 122a. Surfaces 122a also extend down the sides of distal tip region 34 until they reach molding 38. Between surfaces 120a and 122a, a porous substrate 124 defines a porous surface 124a for promoting tissue ingrowth and fixation. Surface 124a also extends down the sides of distal tip 34 much as surfaces 122a.

The separation between pacing electrode 120 and sensing electrode 122 is best shown in FIG. 21. Molding 38 has central passage 126, through which a first helical conductor 128 passes and extends substantially until the distal end of molding 38. Conductor 128 has an external diameter corresponding to the internal diameter of passage 126. Electrode portion 122 comprises a hollow cylindrical shaft 122a for extending partially into passage 126 from the distal end of molding 38. Extension 122a has an external diameter sufficient to fit within and establish an electrical connection with conductor 128. Extension 122a also has an internal diameter calculated to surround a hollow shaft 124a of porous part 124. Hollow shaft 124a extends into central passage 126 past extension 122a. Hollow shaft 124a of porous part 124 has an internal diameter calculated to fit around a shaft 120a of pacing electrode 120a. Shaft 120a extends into central passage 126 beyond hollow shaft 124a.

A second helical pacing conductor 130 surrounds a portion of shaft 120a jutting beyond hollow shaft 122a and establishes an electrical connection therewith. An insulating sheath 132 is disposed coaxially within lead 30 between conductors 128 and 130. Insulating sheath 132 extends toward electrode 122 and coaxially surrounds a portion of hollow shaft 124a jutting beyond extension 122a.

In the eighth embodiment shown in FIGS. 21 and 22, pacing surface 120a is designed to have a relatively small surface area (less than 4 mm$^2$) in contact with heart tissue in order to increase pacing impedance. Sensing surface 122a is preferably designed to define a larger surface area in contact with heart tissue, in order to decrease sensing impedance; this can be further improved by providing an enhanced microstructure 122b on the surface of electrode 122, e.g. through texturing or the like. The sensing and pacing operations could be interchanged relative to electrodes 120, 122 or the two electrodes could be used together such as to perform singularly a sensing or pacing function.

FIG. 23 is a fragmentary sectional view of an implantable lead 30, particularly distal tip region 34, in accordance with a ninth preferred embodiment of the present invention. The ninth embodiment comprises an electrode 134 having a hollow shaft 134a extending into axial space 44. Helical conductor 46 extends within hollow shaft 134a and is held in place with the aid of a support pin 136. Electrode 134 extends outward from the distal end of molding 38 with substantially the same diameter as axial space 42 and ends in a mushroom-shaped cap. A porous substrate 138 is an annulus which surrounds the portion of electrode 134 having the same internal diameter as axial space 44. Porous part 138 is seated between the distal end of molding 38 and the mushroom cap of electrode 134.

Figure 24:
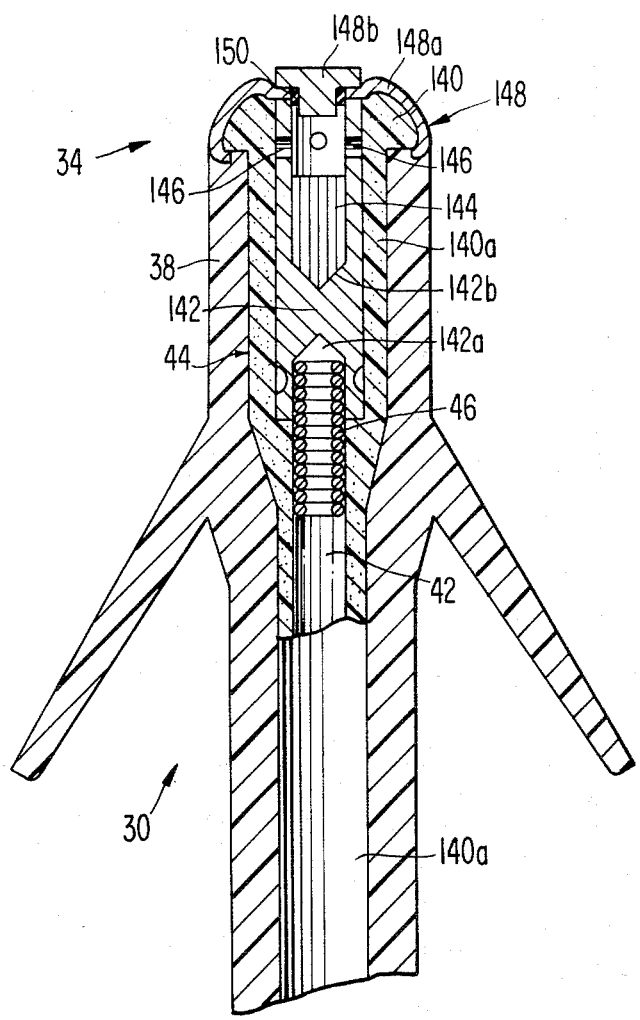
FIG. 24 is a fragmentary sectional view of an implantable lead, illustrating a distal tip region in accordance with a tenth preferred embodiment of the present invention.

FIG. 24 is a fragmentary sectional view of an implantable lead 30, particularly distal tip region 34, in accordance with a tenth preferred embodiment of the present invention. The tenth embodiment comprises a mushroom-shaped porous part 140 having a hollow stem 140a extending from the distal end of molding 38 through axial space 44 and into axial passage 42. Porous part 140 has a mushroom-shaped cap which is seated on the distal end of molding 38. Central hollow stem 140a is coaxial within axial passage 42 in the region of space 44. A crimp tube 142 is disposed within hollow stem 140a in the region of axial space 44. At its proximal end, crimp tube 142 has axial recess 142a for engaging and establishing an electrical connection with helical conductor 44. At its distal end, crimp tube 142 has a second axial recess 142b which extends from within axial space 44 to where hollow stem 140a emerges from the cap of the porous substrate 140.

A bio-active agent delivery device 144 is disposed within recess 142b. Crimp tube 142 has channels 146 leading from porous part 140 into recess 142b in the vicinity of bio-active agent delivery device 144.

An electrode 148, including electrode leaves 148a is in contact with the distal end of crimp tube 142. Electrode leaves 148A bend around the mushroom-shaped cap of porous part 140, and are crimped underneath the cap and at the distal end of molding 38. An electrode plug 148b is provided to crimp leaves 148a onto crimp tube 142 and, to seal space 142b, an elastomeric "O" ring 150 made of bio-compatible material such as silicone rubber is provided.

Figure 25:
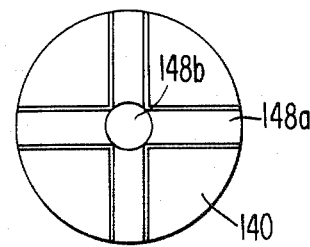
FIG. 25 is a top plan view of the distal tip of FIG. 24.

FIG. 25 is a top view of distal tip region 34 of FIG. 24. Electrode leaves 148a and electrode plug 148b combine to form an electrode surface for stimulating heart tissue and sensing heart contractions. A surface of porous part 140 is also exposed to the surrounding tissue and serves to promote tissue in growth.

An important feature of the tenth embodiment is the incorporation of bio-active agent elution means. Bioactive agent is eluted from bio-active agent delivery device 144 into recess 142b and passages 146. The agent is dispersed through porous part 140 by means of the channels 146. "O" ring 150 seals recess 142b, so that bio-active agent is not eluted directly into the tissue.

The agent delivery device can be any available means of drug delivery, but preferably comprises a polymeric structure containing the agent. Possible materials for the polymeric structure are silicone rubber, ethyl and vinyl acetate and their copolymers, poly(hydroxyethyl) methacrylate (HEMA, or POLYHEMA) and its derivatives and copolymers, polyurethane or other appropriate bio-compatible materials. The pore size of porous part 140 is selected to insure an optimal elution rate. The agent is selected to minimize the formation of fibrous capsule around the implant. The agent may be an anti-inflammatory drug, or, alternatively an agent that preferentially promotes growth of cardiac cells toward the implant, i.e. a growth factor, or an agent that alters the biochemical nature of fibrous capsule, i.e. a collagen modifier.

While a number of different embodiments have been introduced by FIGS. 1-25, it is intended that the disclosed concepts can be interchanged from design to design. All such modifications are considered to fall within the scope of the present invention.

Additional advantages and modifications will readily occur to those skilled in the art. The invention in its broader aspects is, therefore, not limited to the specific detail, representative apparatuses and illustrative examples shown and described. Accordingly, departures may be made from such details without departing from the spirit or scope of the applicant's general inventive concept.

What is claimed is:

1. An implantable stimulating lead for a cardiac pacemaker having a proximal end adapted to be connected to a pulse generator and a distal tip region having a surface area adapted to physically contact heart tissue for stimulating heart tissue in-growth, sensing heart contractions and promoting tissue ingrowth, said distal tip region comprising:

a first member defining a conductive electrode having a conductive first surface area forming a first portion of said distal tip surface area, to stimulate heart tissue and sense heart contractions; and a second member defining a non-conductive substrate having a second surface area forming a second portion of said distal tip surface area for promoting tissue ingrowth, and attachment of said distal tip to heart tissue, said second member including a soluble compound disposed in said substrate for rendering said substrate non-porous until after implantation in the heart tissue whereupon said compound dissolves so as to render said substrate and said second surface area porous.

2. A lead according to claim 1, wherein said soluble compound comprises a bioactive agent dispersed in said substrate, said agent diffusing out of said substrate into the heart tissue so as to render said substrate porous.

* * * * *